United States Patent [19]

Avar et al.

[11] 4,415,687

[45] Nov. 15, 1983

[54] ORGANIC COMPOUNDS

[75] Inventors: Lajos Avar, Biel-Benken, Switzerland; Evelyne Kalt, Riedisheim, France; Hellmuth Reinshagen, Heitersheim, Fed. Rep. of Germany

[73] Assignee: Sandoz Ltd., Basel, Switzerland

[21] Appl. No.: 394,399

[22] Filed: Jul. 2, 1982

[30] Foreign Application Priority Data

| Jul. 6, 1981 [DE] | Fed. Rep. of Germany | 3126604 |
| Aug. 17, 1981 [DE] | Fed. Rep. of Germany | 3132420 |
| Dec. 10, 1981 [DE] | Fed. Rep. of Germany | 3148921 |

[51] Int. Cl.$^3$ .................. C08K 5/34; C07D 251/19; C07D 211/32
[52] U.S. Cl. .................. 524/102; 524/101; 524/103; 546/234; 546/236; 546/237; 546/239; 544/219
[58] Field of Search .............. 546/186, 189, 190, 192, 546/236, 237, 234, 239; 524/89, 90, 100, 102, 103; 106/287.2; 428/423.1, 458, 461

[56] References Cited

U.S. PATENT DOCUMENTS

| 4,251,435 | 2/1981 | Son et al. | 524/102 |
| 4,315,848 | 2/1982 | Dexter et al. | 524/102 |
| 4,356,287 | 10/1982 | Loffelman et al. | 524/99 |

*Primary Examiner*—John Kight, III
*Assistant Examiner*—Kriellion Morgan
*Attorney, Agent, or Firm*—Gerald D. Sharkin; Richard E. Vila; Frederick H. Weinfeldt

[57] ABSTRACT 1,3-dihydroxy-4,6-bis-4'-(2',2',6',6',-tetramethylpiperidyl) benzene, its 1'-alkyl or 1'-(substituted alkyl) derivatives and monomeric or polymeric products derived from these compounds by substitution of 1- and 3-hydroxy groups and/or by the linking of hydroxy groups on adjacent units through a bridging groups, are useful as light and heat stabilizers for polymeric organic materials.

Corresponding bis(3',4'-dehydro) unsaturated compounds are useful as intermediates.

17 Claims, No Drawings

ORGANIC COMPOUNDS

This invention relates to polyalkylpiperidine derivatives, which are useful as light and heat stabilizers for polymeric organic materials.

The invention provides 1,3-dihydroxy-4,6-bis-4'-(2',2',6',6'-tetramethylpiperidyl)benzene, its 1'-alkyl or 1'-(substituted alkyl) derivatives and monomeric or polymeric products derived from these compounds by substitution of 1- and 3-hydroxy groups and/or by the linking of hydroxy groups on adjacent units through a bridging group.

More specifically, the invention provides compounds of formula I

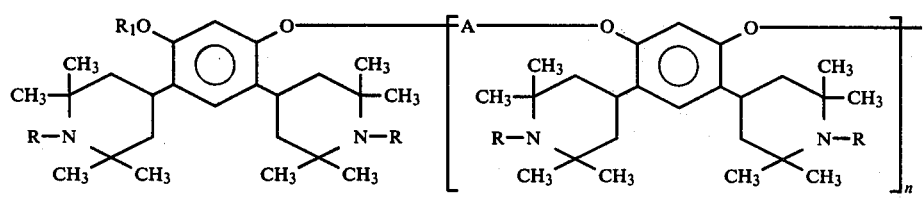

in which
R is hydrogen, $C_{1-12}$alkyl unsubstituted or substituted by one hydroxy or —COO($C_{1-8}$alkyl) group; allyl or benzyl;

n is 0 or 1-20;

A is $C_{2-18}$alkylene or a group (a)-(c)

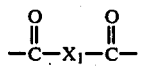 (a)

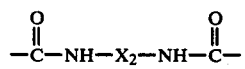 (b)

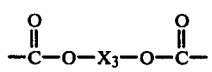 (c)

in which
$X_1$ is a direct bond, $C_{2-14}$alkylene, $C_2$ or $C_3$ alkenylene, hydroxyethylene, $C_{2-20}$alkylene interrupted by oxygen and/or sulphur, phenylene, diphenylene or a polyester group derived from the reaction of a glycol with an excess of a dicarboxylic acid;

$X_2$ is $C_{2-12}$alkylene, phenylene, diphenylene or diphenylenemethane and $X_3$ $C_{2-12}$alkylene, phenylene or

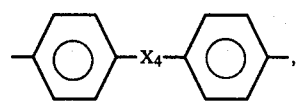

where $X_4$ is methylene, oxygen or —C(CH$_3$)$_2$—; and $R_1$ is hydrogen; $C_{1-20}$alkyl unsubstituted or substituted by ($C_{1-18}$alkoxy)carbonyl, $C_{1-6}$alkoxy or ($C_{1-6}$alkyl)carbonyl; $C_{2-20}$alkenyl; $C_{3-20}$alkynyl; $C_{5-12}$cycloalkyl; phenyl($C_{1-12}$alkyl) or a group of formula

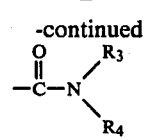 (d)

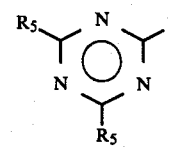 (e)

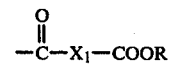 (f)

$$-\overset{O}{\underset{\|}{C}}-X_1-COOR$$ (g)

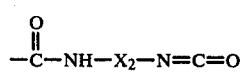 (h)

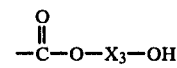 (i)

in which
$R_2$ is $C_{1-20}$alkyl unsubstituted or substituted by ($C_{1-18}$alkoxy)carbonyl, $C_{1-6}$alkoxy or ($C_{1-6}$-alkyl)carbonyl; $C_{2-20}$alkenyl; $C_{3-20}$alkynyl; $C_{5-12}$cycloalkyl; naphthyl; phenyl ($C_{1-12}$alkyl) or phenyl, these phenyl rings being unsubstituted or substituted by one or two $C_{1-8}$-alkyl groups and/or 1 hydroxyl group;

$R_3$ is hydrogen or $C_{1-4}$alkyl;

$R_4$ is hydrogen, $C_{1-20}$alkyl, $C_{5-12}$cycloalkyl, phenyl or naphthyl;

$R_5$ is hydrogen, $C_{1-6}$alkoxy or $C_{1-6}$alkylthio; and

R, $X_1$, $X_2$ and $X_3$ are as defined above.

When any symbol appears more than once in a formula, it may have the same or different significances, unless otherwise stated. When n>1, it may be non-integral, representing an average value.

R as alkyl is preferably $C_{1-4}$alkyl, particularly methyl. Preferably R is hydrogen or alkyl, more preferably hydrogen.

For the monomeric compounds of formula I in which n=O, $R_1$ is preferably $R_{1a}$ where $R_{1a}$ has all of the significances of $R_1$ other than the groups of formula (g), (h) or (i). More preferably it is $R'_{1a}$ where $R'_{1a}$ is $C_{1-20}$alkyl (unsubstituted or substituted as defined above), a group of formula (d) or a group of formula (e). More preferably it is unsubstituted $C_{1-20}$alkyl or a group of formula (d); particularly preferred is a group of formula (d). Preferably both groups $R_1$ are identical.

In the group of formula (d), $R_2$ is preferably $R'_2$ where $R'_2$ is $C_{1-18}$alkyl, allyl, methallyl propargyl, methylpropargyl, cyclopentyl, cyclohexyl, benzyl, α,α-dimethylbenzyl, α-methylbenzyl, phenyl, tolyl, naphthyl, p-t-butylphenyl or

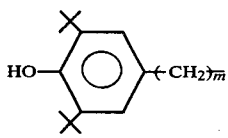

where m is 1 or 2. More preferably, it is $C_{1-18}$-alkyl, particularly $C_{8-18}$alkyl.

In the group of formula (e) $R_3$ is preferably hydrogen and $R_4$ is preferably $C_{1-20}$alkyl or phenyl, more preferably $C_{1-18}$-alkyl, particularly $C_{4-18}$alkyl. In the group of formula (f), $R_5$ is preferably $C_{1-4}$alkoxy.

sulphur. More preferably it is $C_{4-10}$alkylene, particularly those with an even number of carbon atoms, $-CH_2CH_2-S-CH_2CH_2-$ or $-CH_2CH_2-O-CH_2CH_2-$. In the groups of formula (b) and (h), $X_2$ is preferably $C_{2-12}$alkylene, more preferably those with 5, 6, 8, 9, 10, 11 or 12 carbon atoms. In the groups of formula (c) and (i), $X_3$ is preferably $C_{2-6}$alkylene.

For the polymeric compounds of formula I, n is preferably n' where n' is 1–10, more preferably n" when n" is 2–8, particularly 3, 4, 5 or 6.

Preferred monomeric compounds are those of formula Ia and Ia', and preferred polymeric compounds are those of formulae Ib and Ib'

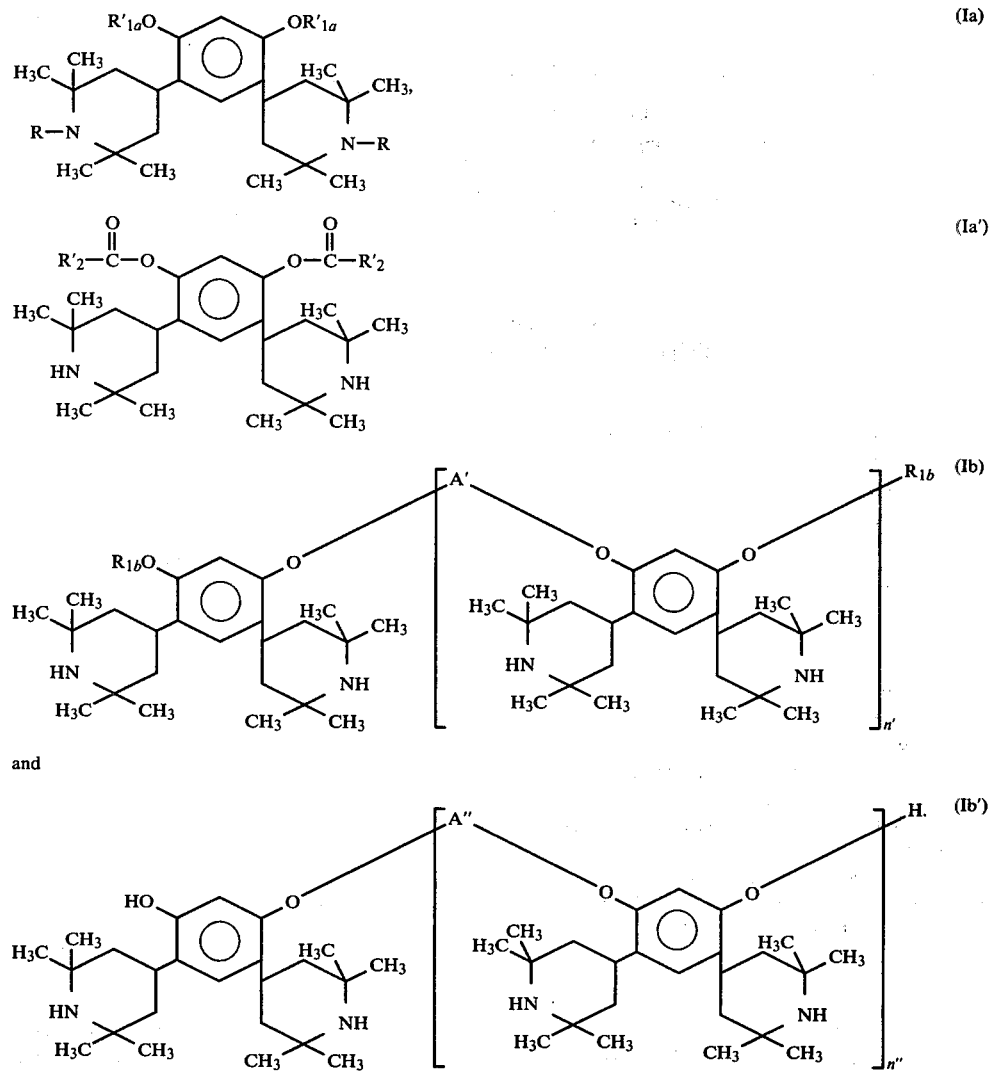

For the polymeric compounds of formula I in which n=1–20, $R_1$ is preferably $R_{1b}$ where $R_{1b}$ is hydrogen, ($C_{1-18}$alkyl)carbonyl or a group of formula (g), (h) or (i). More preferably it is hydrogen or a group (g), (h) or (i), particularly hydrogen.

The bridging group A is preferably A' where A' is a group of formula (a), (b) or (c). More preferably it is A" where A" is a group of formula (a) or (b), particularly a group of formula (a).

In the groups of formula (a) and (g), $X_1$ is preferably $C_{2-12}$-alkylene, which may be interrupted by oxygen or The monomeric compounds of formula I may be prepared in two steps from the compounds of formula II

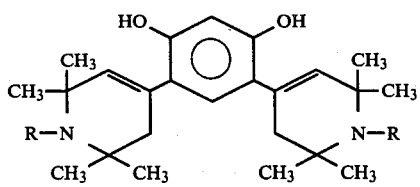

II

Either the compounds of formula II are hydrogenated to the compounds of formula I in which n=0 and both groups $R_1$=H and these compounds are then reacted in known manner with a suitable derivative of the group $R_1$ to be introduced; or the compounds of formula II are reacted in known manner with a suitable derivative of the group $R_1$ to be introduced, and the resulting compounds of formula III

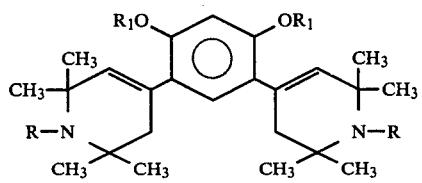

III in which $R_1$ is other than hydrogen, are then hydrogenated.

The intermediate compounds of formulae II and III are novel and also form part of the present invention.

The polymeric compounds of formula I may be prepared by reacting the monomeric compounds of formula I in which both $R_1$'s are hydrogen with a bifunctional derivative of the desired bridging group. Depending upon the ratios of the reagents, the end groups $R_1$ will either be hydrogen or a group derived from reaction of the bifunctional derivative at only one end. Alternatively the polymeric unsaturated products may be obtained from the compounds of formula II and finally hydrogenated.

Thus for the preferred monomeric compounds, where $R_{1a}$ is a substituted or unsubstituted hydrocarbon group, a suitable reagent is $R_1$Hal when Hal is chlorine or bromine. Where $R_1$ is a group (d), then a suitable reagent is $R_2$COOH or a functional derivative thereof. Where $R_1$ is a group (c), a suitable reagent is $R_4$NCO (if $R_3$ is alkyl it may be introduced in a subsequent alkylation step). Finally where $R_1$ is a group (f), this may be introduced by reaction with

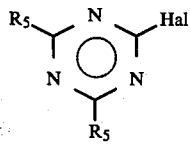

For the preferred polymeric compounds, when the bridging group A is a group of formula (a), this may be introduced by reaction with HOOC—$X_1$—COOH or a functional derivative thereof. When the bridging group is of formula (b), a suitable reagent is OCN—$X_2$—NCO. Finally, where the bridging group is of formula (c), the reagent is prepared by reacting HO—$X_3$—OH with phosgene to obtain

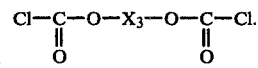

These reagents may also give rise to $R_1$ groups of formulae (g), (h), and (i) respectively.

The compounds of formula II may be obtained by the reaction of 1 mole of resorcinol with 2 moles of triacetonamine in acid medium; followed if required by an N-alkylation step.

Compounds of formula I are useful as stabilizers to protect polymeric organic materials against degradation by light and heat. The concentration of compound of formula I employed in the polymeric material is suitably 0.01 to 5% by weight, preferably 0.02 to 1% by weight. The compound may be added before, during or after the polymerization step, and may be added in solid form; in solution, or as a solid master-batch composition containing 20–80% by wt. of compound of formula I, preferably 40–60%, and 80–20% preferably 60–40% by wt. of a solid polymeric material which is identical with or compatible with the polymeric material to be stabilized.

Suitable polymeric materials include plastics materials for example polyethylene, polypropylene, ethylene/propylene copolymers, polyvinyl chloride, polyester; polyamide, polyurethane, polyacrylonitrile, ABS, terpolymers of acrylates, styrene and acrylonitrile, styrene/acrylonitrile and styrene/butadiene. Other plastics materials such as polybutylene, polystyrene, chlorinated polyethylene, polycarbonate, polymethylmethacrylate, polyphenylene oxide, polypropylene oxide, polacetals, phenol/formaldehyde resins and epoxy resins and epoxy resins may also be used. Preferred plastics materials are polypropylene, polyethylene, ethylene/propylene copolymers and ABS. Natural polymers for example natural rubber may also be stabilized, as may lubricating oils containing polymeric material.

The compounds of formula I may be incorporated by known methods into the polymeric material to be stabilized. Of particular importance is blending of the compounds with thermoplastic polymers in the melt, for example in a melt blender or during the formation of shaped articles, including foils, tubes, fibres and foams by extrusion, injection moulding, blow moulding, spinning or wire coating.

It is not essential for the polymeric material to be fully polymerised before mixing with the compounds according to the invention. The compounds may be mixed with monomer, prepolymer or precondensate, and the polymerisation or condensation reaction carried out subsequently. This will of course be the preferred method of incorporation of the compounds into thermosetting polymers, which cannot be melt blended.

The compounds of formula I may be used alone or in combination with other stabilizers, for example antioxidants. Examples include sterically hindered phenols, sulphur or phosphorus-containing compounds or mixtures of these. Examples are benzofuran-2-ones; indolin-2-ones and sterically hindered phenols such as β-(4-hydroxy-3,5-ditert.-butylphenyl)-propionyl stearate, methane tetrakis-[methylene-3(3',5'-ditert.butyl-4-hydroxyphenyl)-propionate], 1,3,3-tris-(2-methyl-4-hydroxy-5-tert.-butylphenyl)-butane, 1,3,5-tris(4-tert.-butyl-3-hydroxy-2,6-dimethylbenzyl)-1,3,5-triazin-2,4,6 (1H, 3H, 5H)-trione, bis(4-tert.-butyl-3-hydroxy-2,6-dimethylbenzyl)dithiolterephthalate, tris(3,5-ditert.- butyl-4-hydroxybenzyl) isocyanurate, the triester of β-(4-hydroxy-3,5-ditert.-butylphenyl) propionic acid with 1,3,4-tris-(2-hydroxyethyl)-5-triazin-2,4-6(1H, 3H, 5H)-trione, bis[3,3-bis-(4'-hydroxy-3-tert.butylphenyl)-butyric acid] glycol ester, 1,3,5-trimethyl-2,4,6-tris-(3,5-ditert.-butyl-4-hydroxybenzyl) benzene, 2,2'-methylene-bis-(4-methyl-6-tert.-butylphenyl) terephthalate, 4,4-methylene-bis-(2,6-ditert.-butylphenol), 4,4'-butylidene-bis-(tert.-butyl-meta-cresol), 4,4-thio-bis(2-tert.-butyl-5-methyl-phenol), 2,2'-methylene-bis-(4-methyl-6-tert.-butylphenol).

Sulphur-containing antioxidative co-stabilizers which may be used include for example distearylthiopropionate, dilaurylthiodipropionate, methane tetrakis (methylene-3-hexylthiopropionate), methane tetrakis (methylene-3-dodecylthiopropionate) and dioctadecyldisulphide. Phosphorus-containing co-stabilizers include for example trinonylphenyl phosphite, 4,9-distearyl-3,5,8,10-tetraoxadiphosphaspiroundecane, tris-(2,4-ditert.-butylphenyl)phosphite and tetrakis (2,3-ditert.butylphenyl)-4,4'-biphenylylene diphosphonite. Further additives such as aminoaryl compounds and UV-absorbers and light stabilizers e.g. 2-(2'-hydroxyphenyl)-benzotriazole, 2-hydroxybenzophenone, 1,3-bis-(2'-hydroxybenzoyl)-benzene, salicylates, cinnamates, benzoates and substituted benzoates, sterically hindered amines and oxalic acid diamides may be used. Other known types of additives, e.g. flame retardants and antistatic agents, may also be added.

The compounds of formula I are especially suitable for use in organic polymer-containing coatings, particularly automotive finishes.

Automotive finishes are generally solutions or dispersions of organic polymers or polymer precursors in organic solvents. The majority are stoving finishes, which require the application of heat, generally above 100° C., in order to harden the finish in an acceptable time once it has been applied to the primer-coated metal surface. The effect of this heating may be to accelerate the chemical reaction between polymer precursors in a thermosetting system, or to bring about fusion of particles of a thermoplastic polymer.

Many automotive finishes are metallic finishes, which contain flakes of metal, usually aluminum, in order to provide optical effects due to reflection. Such finishes are often two-coat finishes, in which a clear top coat is applied over a base coat containing the pigment and metal flakes. Such two-coat metallic finishes have particular need of UV stabilizers in the top coat, since the polymer in this coat is not protected by light-absorbing pigments, and it is subjected to almost double the normal amount of radiation because of reflection of light from the lower metallic layer.

The compounds of formula I are particularly useful in stoving finishes, particularly in the top coat of two-layer metallic finishes.

The compounds of formula I are suitable for use as UV stabilizers in a wide range of liquid finishes, for example those based on combinations of melamine-formaldehyde resins with oil-modified polyester resins, polyacrylate resins with added crosslinkers, or saturated polyesters; or on self-crosslinked polyacrylate or polyacrylate resin copolymerised with styrene.

Further examples are two-component finishes based on an aliphatic or aromatic di-isocyanate and a hydroxy group-containing polyacrylate, polyester or polyether resin. Thermoplastic polyacrylate resins may also be used, the latter being particularly useful in metallic finishes, as are also polyacrylate resins with added crosslinkers in combination with melamine-formaldehyde resins etherified with butanol and, further, hydroxy group-containing polyacrylate resins hardened with aliphatic di-isocyanates.

The compound of formula I may be added to the finish at any stage in its manufacture, and may be added in solid form or in solution, preferably in the form of a liquid concentrate in a suitable solvent.

The addition of from 0.02–5% by weight, preferably 0.2–2% by weight of one or more compounds of formula I gives a clear improvement in the light- and weather-stability of organic pigments in stoving finishes as well as reducing the tendency to hairline cracking and loss of gloss as the result of weathering. This is surprizingly also found for metallic finishes, and excellent long-term stability of the clear top coat of two-layer metallic finishes is obtained. In such finishes, the compound of formula I may be added to the metallic undercoat, the clear top coar or both, preferably only to the clear top coat.

The following Examples illustrate the invention.

EXAMPLE 1

Into a solution of 5.6 g resorcinol (98%) and 20.8 g triacetonamine hydrochloride in 65 ml glacial acetic acid at 80° C. is passed HCl gas for approx. 8 hours. Finally the mixture is allowed to stand at room temperature for 16 hours, and the solid precipitate is separated by filtration, giving 22.8 g of a white product. This is dissolved in a little water on warming, and the free base is precipitated by addition of 10% sodium carbonate solution, giving resorcinol-4,6-bis-4'-(3',4'-dehydro-2',2',6',6'-tetramethylpiperidine), m.p. 251°–253° C.

EXAMPLE 2

To a solution of 4.3 g of the product of Example 1 in 50 ml dry piperidine is added, at 70° C. and under nitrogen, 9.0 g stearoyl chloride. After stirring at 85° C. for approx. 30 hours the piperidine is distilled off. On addition of 150 ml ether the product is obtained in solid form as the hydrochloride. The precipitate is isolated by filtration, giving 8.4 g of a beige powder, which is taken up in chloroform and made alkaline by washing with 10% sodium carbonate solution. The chloroform layer is then washed with water, treated with silica earth and evaporated to dryness under reduced pressure. The residue is dissolved in benzene, allowed to stand overnight and again filtered. After evaporation of the benzene under reduced pressure there is obtained 9.2 g of 1,3-distearoyloxy-4,6-bis-4'-(3',4'-dehydro-2',2',6',6'-tetramethylpiperidyl)-benzene in the form of a yellow syrup.

EXAMPLE 3

A solution of sodium ethoxide is prepared by adding 1.15 g sodium metal to 100 ml absolute ethanol, and 9.6 g of the product of Example 1 and 10 g octyl bromide (98%) are added at 80° C. After stirring 19 hours at 80° C. the solution is filtered and the mother liquor evaporated. The product, resorcinol-4,6-bis-4'-(3',4'-dehydro-2',2',6',6'-tetramethylpiperidine)dicotyl ether, is isolated by column chromatography as a syrup.

EXAMPLES 4–13

By analogy with Examples 1, 2 and 3, products of formula

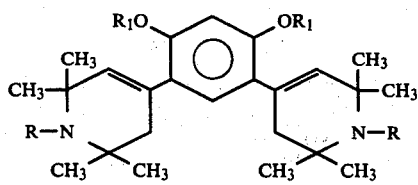

may be obtained, in which both R's and both $R_1$'s are the same and have the significances shown in Table I.

TABLE I

| Example No. | R | $R_1$ | m.p. °C. |
|---|---|---|---|
| 4 | H | —C(=O)—C7H15 | Syrup |
| 5 | H | —C(=O)—C11H23 | Syrup |
| 6 | H | —C(=O)—C6H4—C(CH3)3 | 82–83 |
| 7 | H | —C(=O)(CH2)2—C6H2(C(CH3)3)2—OH | 88–90 |
| 8 | CH3 | —C(=O)—C11H23 | Resin |
| 9 | CH3 | H | 214–215 |
| 10 | H | —C(=O)—C6H4— | 143–144 |
| 11 | H | —C(=O)—CH3 | 149–150 |
| 12 | H | —C(=O)—NHC4H9 | 173–176 |
| 13 | —CH2COOC2H5 | —CH2—COOC2H5 | 103–105 |

EXAMPLE 14

10 g of the product of Example 2 is dissolved in 150 ml glacial acetic acid and allowed to stand for 1 hour over 1.5 g Raney nickel. The nickel catalyst is removed by filtration and the solution is then hydrogenated at room temperature and 10 atm. pressure in the presence of 3.0 g 5% palladium on active charcoal. When uptake of hydrogen has ended, the catalyst is filtered off and the filtrate evaporated to dryness and made alkaline by addition of 10% sodium carbonate. The product is resorcinol-4,6-bis-4'-(2',2',6',6'-tetramethylpiperidine), m.p. >300° C.

EXAMPLES 15–26

By hydrogenation in analogous manner to Example 14, the products of Examples 2–13 may be converted to the corresponding compounds having saturated piperidine rings.

EXAMPLE 27

9.6 of the product of Example 14 is dissolved in 600 ml pyridine at 80° C., and 32.4 g stearoyl chloride is added at this temperature. After stirring 22 hours at 85° C., the pyridine is is distilled off. On addition of benzene the product is precipitated as the hydrochloride. The precipitate is separated, dissolved in hot water in the presence of ethyl acetate and made alkaline with 10% aqueous sodium carbonate. The organic phase is separated, evaporated and the residue taken up in acetone, filtered and dried, giving 1,3-distearoyloxy-4,6-bis-4'-(2',2',6',6'-tetramethylpiperidinyl)benzene in the form of a resin.

EXAMPLE 28

19.4 g of the product of Example 14 and 20.3 g n-octyl bromide are added to 2.3 g sodium in 100 ml absolute alcohol. After stirring at 80° C. for 67 hours the mixture is filtered hot and the filtrate cooled. The resulting precipitate is isolated, taken up in hexane and decolorised. After evaporation of solvent there is obtained resorcinol-4,6-bis-4'-(2',2',6',6'-tetramethylpiperidine)dioctyl ether, m.p. 73°–77° C.

EXAMPLES 29–31

By analogy with Examples 27 and 28, products of formula

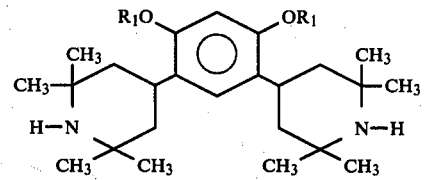

may be obtained, in which both $R_1$'s are the same and have the significance shown in Table II.

TABLE II

| Example No. | $R_1$ | m.p. °C. |
|---|---|---|
| 29 | —C11H23 | resin |
| 30 | —COCH3 | 206–7 |
| 31 | —CO—C6H4—C(CH3)3 | 211–213 |

EXAMPLE 32

6.76 g of the product of Example 14 in the form of its diacetate and 2.95 g sebacic acid (98%) are stirred together under nitrogen for 2 hours at 200° C. The acetic acid which is liberated during the reaction is collected. The reaction mixture is then stirred for a further 6 hours at 180° C. under a vacuum of 1 mm Hg.

The product is a poly-resorcinol-4,6-bis-4'-(2',2',6',6'-tetramethylpiperidine) sebacate, m.p. 129°–131° C., molecular weight 2400 as determined by vapour pressure measurement.

EXAMPLE 33

By analogy with Example 32, but using adipic acid in place of sebacic acid, the corresponding polymeric adipate is obtained, m.p. 158°–165° C. MW 1670.

EXAMPLE 34

By analogy with Example 32, but using n-decane-1,10-dicarboxylic acid in place of sebacic acid, the corresponding polymeric decane, 1,10-dicarboxylate is obtained, m.p. 127°–130° C., MW 2320.

APPLICATION EXAMPLE A 0.5% by wt. of the compound of Example 27 is worked into polypropylene (containing no UV stabilizer) in a kneading mixer at 180° C. The resulting mass is pressed into a 3 mm thick plate, and also into a 0.3 mm thick film. The film is illuminated in an Atlas Weatherometer WRC 600 with a xenon lamp, and the damage caused by UV light is measured by the growth in intensity of the IR carboxyl band absorption at 5.8μ. According to test method DIN 53453, the change in impact strength of samples cut from the 3 mm plate is measured after exposure in the Atlas Weatherometer. In both cases the results obtained are better, than those using unstabilized polymer.

APPLICATION EXAMPLE B

A two-layer metallic finish is prepared having the following composition:

Base Coat 12.6 parts commercial polyacrylate resin, with added crosslinking as defined in DIN 53 186 (Viacryl, SC 344, Vianova, Vienna, supplied as 50% solution in xylene/-butanol 4:1)
2.19 parts commercial butanol-etherified melamine resin, medium reactive, prepared by condensation of 1 mol melamine with 3–6 mole formaldehyde, etherified with 3–6 mole butanol according to DIN 53 187 (Maprenal MF 800, Casella, supplied as 72% solution in isobutanol)
0.96 parts butanol
0.26 parts colloidal silicic acid
7.05 parts xylene
52.0 parts of a 20% cellulose acetate butyrate solution of the following composition by weight:
   20% cellulose acetate butyrate: acetyl content 13.6%, butyryl content 38.7%, hydroxyl content 1.25%, viscosity of 20% solution in acetone=200 cp
   10% butanol
   35% xylene
   35% butyl acetate
6.80 parts non-leafing aluminium paste, supplied as 65% suspension in alkylglycol acetate according to DIN 55 923
18.14 parts butyl acetate
0.3 parts copper phthalocyanine blue (C.I. Pigment Blue 15:1)

(b) Top Coat 80.00 parts polyacrylate resin (as in the base coat)
13.75 parts melamine resin (as in the base coat)
4.50 parts butyl glycollate
7.50 parts aromatic hydrocarbon solvent, b.p. 186°–212° C.
6.00 part aromatic hydrocarbon solvent, b.p. 155°–178°

(c) Application

The base coat is applied to primer-coated metal plates by spraying, giving a layer approx. 20 μm thick, without UV stabilizer. After drying of the base coat, the plates are sprayed with
(i) top coat as in (b) above, without UV stabilizer or
(ii) top coat as in (b) above, containing 1 part (i.e. 1% by wt.) of the compound of Example 27, added as an 80% solution in xylene, and stoved at 140° for 30 minutes. Exposure tests (1 year in Florida) show superior results for the plates coated with top coat (ii).

The compounds of Examples 14–26 and 28–34 can be used in analogous manner to Application Examples A and B.

We claim:

1. 1,3-dihydroxy-4,6-bis-4'-(2',2',6',6'-tetramethyl-piperidyl) benzene, its 1'-alkyl or 1'-(substituted alkyl) derivatives and monomeric or polymeric products derived from these compounds by substitution of 1- and 3-hydroxy groups and/or by the linking of hydroxy groups on adjacent units through a bridging group.

2. A compound of formula I

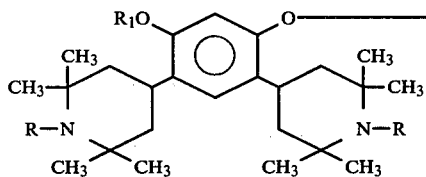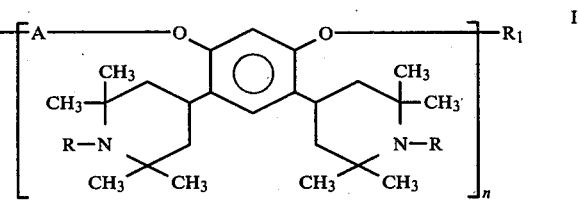

in which
R is hydrogen, $C_{1-12}$alkyl unsubstituted or substituted by one hydroxy or —$COO(C_{1-8}alkyl)$ group; allyl or benzyl;
n is 0 or 1–20;
A is $C_{2-18}$alkylene or a group (a)–(c)

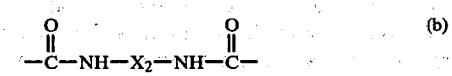

in which
$X_1$ is a direct bond, $C_{2-14}$alkylene, $C_2$ or $C_3$ alkylene, hydroxyethylene, $C_{2-20}$alkylene interrupted by oxygen and/or sulphur, phenylene, diphenylene or a polyester group derived from the reaction of a glycol with an excess of a dicarboxylic acid;

$X_2$ is $C_{2-12}$alkylene, phenylene, diphenylene or diphenylenemethane and
$X_3$ $C_{2-12}$alkylene, phenylene or

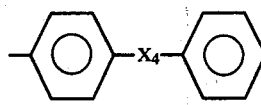

where
$X_4$ is methylene, oxygen or —$C(CH_3)_2$—; and
$R_1$ is hydrogen, $C_{1-20}$alkyl unsubstituted or substituted by ($C_{1-18}$alkoxy)carbonyl, $C_{1-6}$alkoxy or ($C_{1-6}$alkyl)carbonyl; $C_{2-20}$alkenyl; $C_{3-20}$alkynyl; $C_{5-12}$cycloalkyl; phenyl($C_{1-12}$alkyl) or a group of formula

 (d)

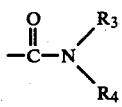 (e)

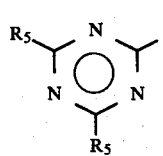 (f)

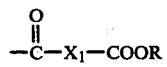 (g)

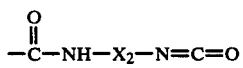 (h)

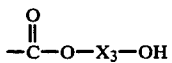 (i)

in which
$R_2$ is $C_{1-20}$alkyl unsubstituted or substituted by ($C_{1-18}$alkoxy)carbonyl, $C_{1-6}$alkoxy or ($C_{1-6}$alkyl)carbonyl; $C_{2-20}$alkenyl; $C_{3-20}$alkynyl; $C_{5-12}$cycloalkyl; phenyl ($C_{1-12}$alkyl) or phenyl, these phenyl rings being unsubstituted or substituted by one or two $C_{1-8}$-alkyl groups and/or 1 hydroxyl group;
$R_3$ is hydrogen or $C_{1-4}$alkyl;
$R_4$ is hydrogen, $C_{1-20}$alkyl, $C_{5-12}$cycloalkyl, phenyl or naphthyl;
$R_5$ is hydrogen, $C_{1-6}$alkoxy or $C_{1-6}$alkylthio; and
R, $X_1$, $X_2$ and $X_3$ are as defined above.

3. A compound according to claim 2 in which n=0.
4. A compound of formula Ia

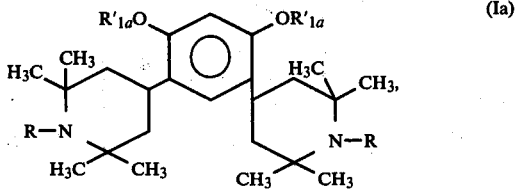 (Ia)

in which
R is defined in claim 2 and
$R'_{1a}$ is $C_{1-20}$alkyl, unsubstituted or substituted as defined in claim 2, or a group of formula (d) or (e), defined in claim 2.

5. A compound of formula Ia'

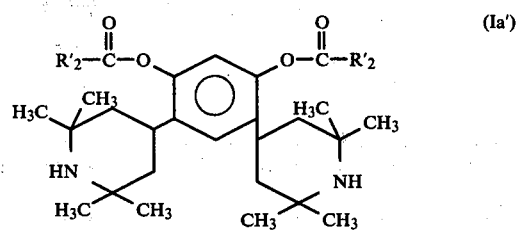 (Ia')

in which $R'_2$ is $C_{1-18}$alkyl, allyl, methallyl, propargyl, methylpropargyl, cyclopentyl, cyclohexyl, benzyl, α,α-dimethylbenzyl, α-methylbenzyl, phenyl, tolyl, naphthyl, p-t.-butylphenyl or

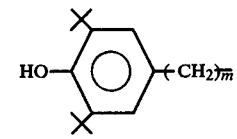

where m is 1 or 2.

6. A compound according to claim 2 in which n is 1–20.

7. A compound of formula Ib

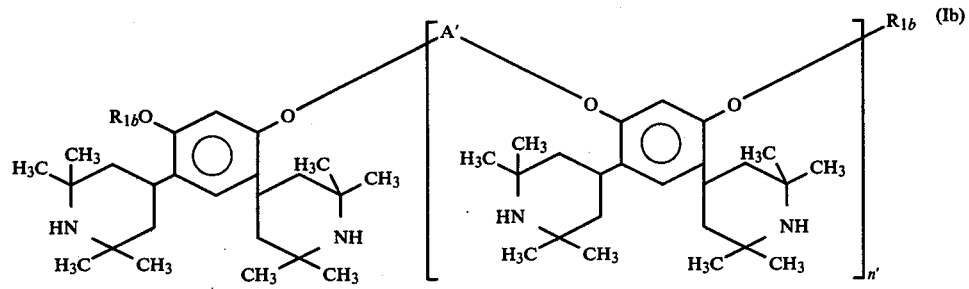 (Ib)

in which
$R_{1b}$ is hydrogen, ($C_{1-18}$alkyl) carbonyl, or a group of formula (g), (h) or (i), defined in claim 2, and
A' is a group of formula (a), (b) or (c), defined in claim 2.

8. A compound of formula Ib'

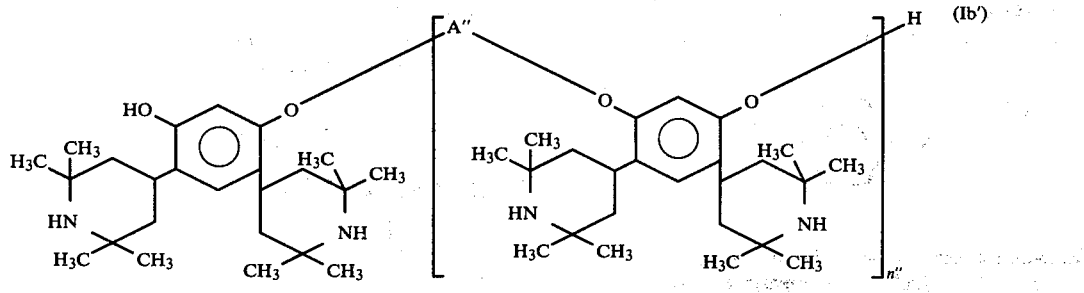

in which A″ is a group of formula (a) or (b), defined in claim 2.

9. A compound of formula

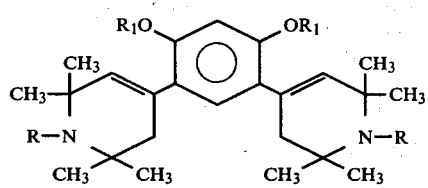

in which R and R₁ are defined in claim 2.

10. A compound according to claim 9 in which $R_1$ is hydrogen.

11. A process for the stabilization of polymeric organic materials against the effects of light and heat comprising the incorporation of from 0.01 to 5% by weight of a compound according to claim 1 into the polymeric material to be stabilized.

12. A polymeric material stabilized against the effects of light and heat, containing from 0.01 to 5% by weight of a compound according to claim 1.

13. A solid masterbatch composition containing 20–80% by weight of a compound according to claim 1 and 80–20% by weight of a solid thermoplastic polymer.

14. A liquid stoving automotive finish for application to a metal surface, containing 0.02–5% by weight of a compound according to claim 1.

15. A liquid stoving automobile finish for application as the clear top coat in a two-layer metallic finish, containing 0.02–5% by weight of a compound according to claim 1.

16. A cured automotive finish obtained by applying and stoving a liquid finish according to claim 14 or 15.

17. A monomeric product of claim 1 which is 1,3-distearoyloxy-4,6-bis-4′(2′,2′,6′,6′-tetramethyl-piperidinyl) benzene.

* * * * *